United States Patent [19]

Autieri

[11] Patent Number: 6,090,580
[45] Date of Patent: Jul. 18, 2000

[54] INTERFERON RESPONSIVE TRANSCRIPT (IRT-1)

[75] Inventor: Michael V. Autieri, Blue Bell, Pa.

[73] Assignee: Temple University of the Commonwealth System of Higher Education, Philadelphia, Pa.

[21] Appl. No.: 09/004,171

[22] Filed: Jan. 2, 1998

[51] Int. Cl.$^7$ .............................. C12P 21/06; C07H 21/04
[52] U.S. Cl. ...................................... 435/69.1; 435/252.33; 435/325; 435/320.1; 530/350; 536/23.1; 536/23.5
[58] Field of Search ........................... 530/350; 536/23.5; 435/69.1, 252.3, 252.33, 320.1, 325

[56] References Cited

U.S. PATENT DOCUMENTS

| 4,419,446 | 12/1983 | Howley et al. | 435/68 |
| 4,946,778 | 8/1990 | Ladner et al. | 435/69.1 |

FOREIGN PATENT DOCUMENTS

| 95/17506 | 6/1995 | WIPO . |

OTHER PUBLICATIONS

Nedwin et al., "Human lymphotoxin and tumor necrosis factor gene: structure homology and chromosomal localization", *Nucl. Acid. Res.*, 1985, vol. 13, No. 17 pp. 6361–6373.

Messer et al., "Polymorphic structure of the tumor necrosis factor (TNF) locus: an NcoI gene polymorphism in the first intron of the human TNF βgen correlates with a variant amino acid in position 26 and a reduced level of TNF–βproduction", *J. Exp. Med.*, Jan. 1991, vol. 173.

Imai et al. "A novel gene iba1 in the major histocompatibility complex class III region . . . " Biochem. BioOphys. Res. Comm. 224, 855–862, 1996.

Autieri et al. IRT–1, a novel interferon–gama–responsive transcript encoding a growth–suppressing basic leucine zipper protein J. Biol. Chem. 273, 14731–14737, Jun. 1998.

Libby et al., "A cascade model for restenosis: a special case of atherosclerosis progression," Circulation 86:III–47–III–52 (1992).

Ross, "The pathogenesis of atherosclerosis: a perspective for the 1990s," Nature 362:801–809 (1993).

O'Brien et al., "Proliferation in primary and restenotic coronary atherectomy tissue," Circ. Res. 73:223–231 (1993).

Clowes et al., "Mechanisms of stenosis after arterial injury," Lab. Invest. 49:208–215 (1983).

Liu et al., "Restenosis after coronary angioplasty: potential biologic determinants and role of intimal hyperplasia," Circulation 79:1374–1380 (1989).

Austin et al., "Intimal proliferation of smooth muscle cells as an explanation for recurrent coronary artery stenosis after percutaneous transluminal coronary angioplasty." J. Am. Coll. Cardiol. 6:369–375 (1985).

Schwartz et al., "Restenosis after balloon angiopalsy: a practical proliferative model in porcine coronary arteries," Circulation 82:2190–2200 (1990).

Nilsson, "Cytokines and smooteh muscle cells in atherosclerosis," Cardiovasc Res 27:1184–1189 (1992).

Tanaka et al., "Cytokine gene regulation: regulatory cis–elements and DNA binding facors involved in the interferon system,"Adv. Immunol. 52:263–281 (1992).

Hansson et al., "T lymphocytes inhibit the vascular response to injury," Proc. Natl. Acad. Sci. USA 88:10530–10534 (1991).

Rolfe et al., "T lymphocytes affect smooth muscle cell phenotype and proliferation," Arterioscler. Thromb. Vasc. Biol. 15:1204–1210 (1995).

Nunokawa et al., "Interferon–inhibits proliferation of rat vascular smooth muscle cells by nitoric oxide generation," Biochem. Biophys. Res. Comm. 188:409–415 (1992).

Tanaka et al., "Recognition DNA sequences of Interferon Regulatory Factor 1 (IRF–1) and IRF–2, Regulators of Cell growth and the Interferon system," Mol. Cell Bio. 13:4531–4538 (1993).

Wang et al., "Interferon Regulatory Factors and TFIIB cooperatively regulate Interferon–responsive promoter activity in vivo and in vitro," Mol. Cell Bio. 16:6313–6324 (1996).

Matthews et al., "Analytical Strategies for the Use of DNA Probes," Anal. Biochem. 169: 1–25 (1988).

Miller et al., Genetic Engineering 8:277–298 (Plenum Press 1986).

Ohlstein et al., Eur. J. Pharmacol.—Mol. Pharmacol. Section 225:347–350 (1992).

Gething et al., Nature 293:620–625 (1981).

Kaufman et al., Mol. Cell. Biol. 5(7):1750–1759 (1985).

Huse et al., Science 246:1275–1281 (1988).

Gram et al. J. Immunol. Meth. 161:169–176 (1993).

Swimmer et al., Proc. Natl. Acad. Sci. USA 89:3756–3760 (1992).

Autieri et al., "cDNA cloning of human Allograft Inflammatory Factor–1: tissue distribution, cytokine induction, and mRNA expression in injured rat carotid arteries," Biochem. Biophys. Res. Comm. 228:29–37 (1996).

(List continued on next page.)

*Primary Examiner*—Nashaat T. Nashed
*Attorney, Agent, or Firm*—Seidel, Gonda, Lavorgna & Monaco, PC

[57] ABSTRACT

An isolated transcribed nucleotide sequence, termed interferon Responsive Transcript -1 (IRT-1), encodes a deduced 132 amino acid basically-charged protein. The invention is directed to IRT-1 nucleic acid, its structural and functional homologs, including portions of the nucleotide, and complements of the nucleotide sequence. Also provided are isolated amino acid sequences encoded by the IRT-1 nucleotide sequences, structural and functional homologs of the isolated amino acid sequences, including portions of the amino acid sequences and antibodies to the amino acid sequences. The IRT-1 nucleic acid sequences may be used to detect and produce other sequences, to regulate or oppose production of vascular smooth muscle cells, and to prevent or treat proliferative arterial disease and/or vascular restenosis.

11 Claims, 4 Drawing Sheets

OTHER PUBLICATIONS

Autieri et al., "Use of Differential Display to Identify Differentially Expressed mRNAs Induced by Rat Carotid Artery Balloon Angioplasty," Lab. Invest. 72:656–671 (1995).

Hansson et al., "Immune mechanisms in atherosclerosis," Arteriosclerosis 9:567–578 (1989).

Wang et al. "T–cell lymphokines, Interleukin–4, and Gamma Interferon, modulate the induction of vascular smooth muscle tissue plasminogen activator and migration by serum and Platelet–Derived Growth Factor," Circ. Res. 77:1095–1106 (1995).

Hansson et al., "Interferon y inhibits arterial stenosis after injury," Circulation 84:1266–1271 (1991).

Castronuovo et al., "Cytokine therapy for arterial restenosis: inhibition of neointimal hyperplasia by gamma–interferon," Cardiovascular Surgery 3:463–468 (1995).

Banerji et al., "A gene pair from the human major histocompatibility complex encodes large proline–rich proteins with multiple repeated motifs and a single ubiquitin–like domain," Proc. Natl. Acad. Sci. USA 78:2374–2378 (1990).

Iris et al., "Dense Alu clustering and a potential new member of the NF–KB family within a 90 kilobase HLA class III segment," Nature Genetics 3:137–145 (1993).

Altschul et al., "Basic local alignment search tool," J. Mol. Biol. 215:403–410 (1990).

Gish et al., "Identification of protein coding regions by database similarity search," Nature Genetics 3:266–272 (1993).

Cesareni, "Peptide display on filamentous phage capsids," FEBS 11227 307:1 66–70 (Jul. 1992).

Karlin et al., "Applications and statistics for multiple high–scoring segments in molecular sequences," Proc. Natl. Acad. Sci. USA 90:5873–5877 (1993).

Karlin et al., "Methods for assessing the statistical significance of molecular sequence features by using general scoring schemes," Proc. Natl. Acad. Sci. USA 87:2264–2268 (1990).

Kozak, "An analysis of 5' noncoding sequences from 699 vertebrate messenger RNAs,"Nucleic Acids Research, 15:8125–8148 (1987).

Ohlstein et al., "The selective endothelin $ET_A$ receptor antagonist BQ123 antagonizes endothelin–1–mediated mitogenesis,"Molecular Pharmacology, 225:347–350 (1992).

Autieri et al., "Isolation and Characterization of BART–1: A Novel Balloon Angioplasty Responsive Transcript in Rat Carotid Arteries," DNA and Cell Biology, 15:297–304 (1996).

Autieri et al., "Antisense Oligonucleotides to the P65 subunit of NF–kB inhibit human vascular smooth muscle cell adherence and proliferation and prevent neointima formation in rat carotid arteries," Biochemical and Biophysical Research Communications, 213:827–836 (1995).

Utans et al., "Cloning and Characterization of Allograft Inflammatory Factor–1: A Novel Macrophage Factor Identified in Rat Cardiac Allografts with Chronic Rejection," J. Clin. Invest., 95:2954–2962.

```
                                  GAGGAAAAGCTTTCGGACTGCTGAAGGCCCAGCAGGAAGA
  41   GAGGCTGGATGAGATCAACAAGGCAATTCCTAGACGATCCCAAATATAGCAGTGATGAG
 100   GATCTGCCCTCCAAACTGGAAGGCTTCAAAGGTGAGGGGGAAACTGTAGGCGGTGGAGA
 159   CAGGGCTGGGGGTAGGAGGGTTAGGATTTCCACAAGAACAAGGCAGGAACAGCAGAGAT
 218   AAAAAGTTTACTTTTGTGGTAGCAAAAGGGGAACCTGCCTTTATTGCCCTCCTGCCACA
 277   CTGCGGTCCCTTTCCCGGGCCTGCCTCTCTCAGCATCCCCTCTAGCTCCTTACAACCTA
 336   GCGGGGCCCTCAACTCCCAACCCCACTTCCTCTGCCTGCCCCTCCTCCTCCTTCCACGT
 395   TGTCTCCTCCACCTAGCAGTTGGTTGGCAACCCCTTCCTCACCTCACCCAGAGAAATAC
 454   ATG GAG TTT GAC CTT AAT GGA AAT GGC GAT ATT GGT GAG AAA CGG
        M   E   F   D   L   N   G   N   G   D   I   G   E   K   R   15
 499   GTG ATT TGC GGG GGC AGG GTG GTG TGC AGG CCT AAG AAG ACA GAG
        V   I   C   G   G   R   V   V   C  │R   P   K   K│ T   E   30
 544   GTC TCT CCT ACA TGC TCC ATT CCT CAT GAT TTG GGA GGG GGC CCA
        V   S   P   T   C   S   I   P   H   D   L   G   G   G   P   45
 589   CCT ACC ACA GTG GGA GGA AGG AGA ATG GGG ATG CGG AAG TGG GAG
        P   T   T   V   G   G   R   R   M   G   M   R   K   W   E   60
 634   AGG AGA GAG AGG GTC TCC CCA CCT TCT CCC CAT CCC CAT CCT CTG
        R   R   E   R   V   S   P   P   S   P   H   P   H   P   L   75
 679   CCC CCA GAT ATC ATG TCC CTG AAA CGA ATG CTG GAG AAA CTT GGA
        P   P   D   I   M   S   L   K   R   M   L   E   K   L   G   90
 724   GTC CCC AAG ACT CAC CTA GAG CTA AAG AAA TTA ATT GGA GAG GTG
        V   P   K   T   H   L   E   L   K   K   L   I   G   E   V  105
 769   TCC AGT GGC TCC GGG GAG ACG TTC AGC TAC CCT GAC TTT CTC AGG
        S   S   G   S   G   E   T   F   S   Y   P   D   F   L   R  120
 814   ATG ATG CTG GGC AAG ACA TCT GCC ATC CCT AAA ATG TGA GTGTCAA
        M   M   L   G   K   T   S   A   I   P   K   M   *          132
 860   TTTCCAACCTCCCCTGTACTTACCTGTTTTCTCCTCCCCCATCCCTACCCTTGTCCACA
 919   GGCTCAACATTTCTACACGTTGCCCATCATCCCTTCTTCCATCCTTAGAGGGACCCTTC
 978   CAAGGTCCCGACCCCATCCCTATCCATAGTCCTGGTCCCCAGAAACTCCAACCCCTGCC
1037   CTTCCTCTTCCCCCTTCCACCCTCACATCCCATCCCCTTCTAGCCTTTCCTAGCACCC
1096   TATGATTTATTCCCTTGAGAGGAGTGTTCCCTGATCCCTGTGCCTCTTCCCATCTCAAC
1155   CAGGATCCTGATGTATGAGGAAAAAGCGAGAGAAAAGGAAAAGCCAACAGGCCCCCAG
1214   CCAAGAAAGCTATCTCTGAGTT
                                                                    1235
```

Fig. 4A

Fig. 4B
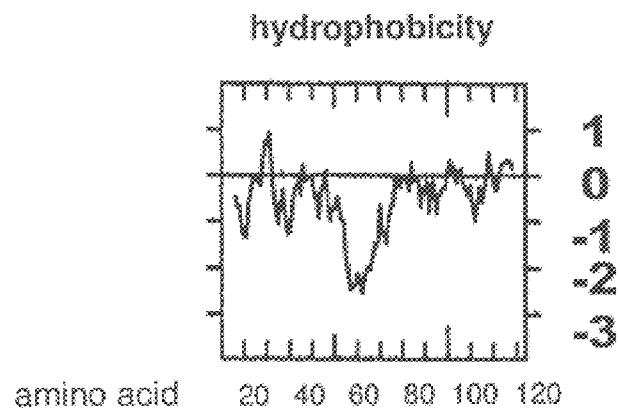
Fig. 4C
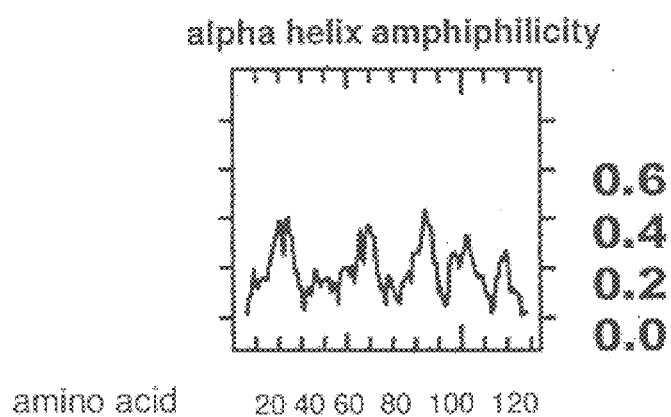
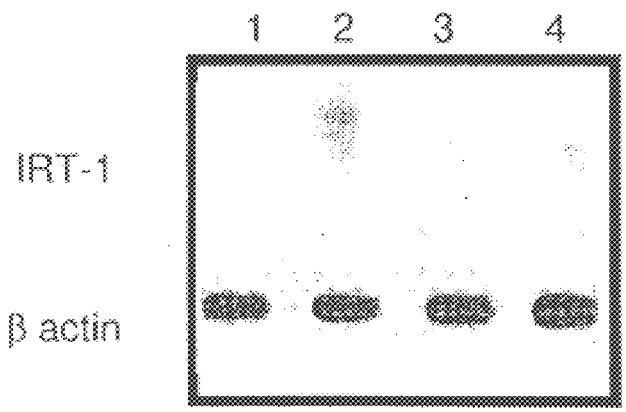
Fig. 5

SEQUENCE LISTING

```
<160> NUMBER OF SEQ ID NOS: 4

<210> SEQ ID NO 1
<211> LENGTH: 1235
<212> TYPE: DNA
<213> ORGANISM: Homo sapiens

<400> SEQUENCE: 1
```

-continued

```
gaggaaaagc tttcggactg ctgaaggccc agcaggaaga gaggctggat gagatcaaca       60
aggcaattcc tagacgatcc caaatatagc agtgatgagg atctgccctc caaactggaa      120
ggcttcaaag gtgaggggga aactgtaggc ggtggagaca gggctggggg taggagggtt      180
aggatttcca caagaacaag gcaggaacag cagagataaa aagtttactt ttgtggtagc      240 aaaagggga cctgccttta ttgccctcct gccacactgc ggtccctttc ccgggcctgc       300
ctctctcagc atcccctcta gctccttaca acctagcggg gccctcaact cccaacccca      360
cttcctctgc ctgcccctcc tcctccttcc acgttgtctc ctccacctag cagttggttg      420 gcaaccccctt cctcacctca cccagagaaa tacatggagt ttgaccttaa tggaaatggc     480
gatattggtg agaaacgggt gatttgcggg ggcaggtgg tgtgcaggcc taagaagaca       540
gaggtctctc ctacatgctc cattcctcat gatttgggag ggggcccacc taccacagtg     600
ggaggaagga gaatggggat gcggaagtgg gagaggagag agggtctc cccaccttct        660 ccccatcccc atcctctgcc cccagatatc atgtccctga acgaatgct ggagaaactt       720 ggagtcccca agactcacct agagctaaag aaattaattg gagaggtgtc cagtggctcc     780
ggggagacgt tcagctaccc tgactttctc aggatgatgc tgggcaagac atctgccatc    840
cctaaaatgt gagtgtcaat ttccaacctc ccctgtactt acctgttttc tcctccccca    900
tccctaccct tgtccacagg ctcaacattt ctacacgttg cccatcatcc cttcttccat    960
ccttagaggg acccttccaa ggtcccgacc ccatccctat ccatagtcct ggtccccaga    1020
aactccaacc cctgcccttc ctcttccccc ttccacccct acatccccat cccccttctag  1080 cctttcctag caccctatga tttattccct tgagaggagt gttccctgat ccctgtgcct    1140
cttcccatct caaccaggat cctgatgtat gaggaaaag cgagagaaaa ggaaaagcca     1200
acaggccccc cagccaagaa agctatctct gagtt                                1235
```

<210> SEQ ID NO 2
<211> LENGTH: 132
<212> TYPE: PRT
<213> ORGANISM: Homo sapiens

<400> SEQUENCE: 2

```
Met Glu Phe Asp Leu Asn Gly Asn Gly Asp Ile Gly Glu Lys Arg Val
  1               5                  10                  15

Ile Cys Gly Gly Arg Val Val Cys Arg Pro Lys Lys Thr Glu Val Ser
             20                  25                  30

Pro Thr Cys Ser Ile Pro His Asp Leu Gly Gly Pro Pro Thr Thr
         35                  40                  45

Val Gly Gly Arg Arg Met Gly Met Arg Lys Trp Glu Arg Arg Glu Arg
     50                  55                  60

Val Ser Pro Pro Ser Pro His Pro His Pro Leu Pro Pro Asp Ile Met
 65                  70                  75                  80

Ser Leu Lys Arg Met Leu Glu Lys Leu Gly Val Pro Lys Thr His Leu
                 85                  90                  95

Glu Leu Lys Lys Leu Ile Gly Glu Val Ser Ser Gly Ser Gly Glu Thr
            100                 105                 110

Phe Ser Tyr Pro Asp Phe Leu Arg Met Met Leu Gly Lys Thr Ser Ala
        115                 120                 125

Ile Pro Lys Met
        130
```

-continued

```
<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Nuclear
      localization sequence in SEQ ID NO:2

<400> SEQUENCE: 3

Arg Pro Lys Lys
  1

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Kozak
      consensus sequence

<400> SEQUENCE: 4
gccgccgcca tgg                                                      13
```

INTERFERON RESPONSIVE TRANSCRIPT (IRT-1)

BACKGROUND OF THE INVENTION

The use of percutaneous transluminal coronary angioplasty (PTCA) to alleviate the myocardial ischemia associated with advanced multi-vessel coronary artery disease has increased exponentially in the past decade. However, the long term efficacy of PTCA is significantly limited by the high incidence of vascular restenosis observed in as many as 40% of patients undergoing this procedure (1). The lack of an effective pharmaceutical modality to retard this process is indicative of the poor understanding of the precise molecular mechanisms underlying the pathophysiology of vascular restenosis.

The resultant neointima formation associated with balloon angioplasty is a complex process actively involving various cell types which secrete many different cytokines and growth factors seminal to the local inflammatory response (2). These cytokines include, but are not limited to, interleukin 1 (IL-1), platelet-derived growth factor (PDGF), and a number of colony stimulating factors (CSFs) and interferons (IFNs) (3,4). The major cellular component of the atherosclerotic lesion is the vascular smooth muscle cell, which, upon exposure to these soluble factors, migrates into the intimal layer and proliferates. In restenotic lesions, VSMCs express a synthetic phenotype and secrete many cytokines and matrix proteins, which further promotes VSMC growth in an autocrine fashion (5,6). It has been suggested that cytokine-induced activation of VSMC in the media resulting in intimal thickening is the most critical cellular event in the restenotic process (5-8).

Interferons, including IFNγ, interact with target cells to induce expression of a number of IFN-specific genes (9). IFNγ-inducible genes manifest their biological activities by anti-viral, immune modulatory, and anti-proliferative effects (10). This is particularly true in VSMC, as it has been shown that proliferation of these cells is inhibited by lymphocyte factors, including IFNγ (11,12). The anti-proliferative effects of IFNγ on VSMC can be exerted indirectly, though generation of nitric oxide (13), or directly, though generation of the Interferon Regulatory Factor (IRF) family of transcriptional regulators, which act as activators or repressors of IFNγ-inducible genes (14,15).

Transcriptional regulators encode transcription factors, which are proteins that directly link external, receptor-mediated events with gene expression. Research has been directed to identifying transcriptional regulators and transcription factors that might play a role in restenosis.

Allograft Inflammatory Factor-1 (AIF-1) is a gene which has been studied to determine what role it might play in the restenotic process. The sequences of rat and human AIF-1 are disclosed in WO 95/17506. AIF-1 is induced by serum and many cytokines.

All references cited herein are incorporated herein by reference in their entireties.

SUMMARY OF THE INVENTION

The invention provides a novel isolated nucleotide sequence, termed IRT-1 (SEQ ID NO:1), structural and functional homologs thereto, including portions thereof, and complements thereto.

The invention also provides a novel isolated amino acid sequence (SEQ ID NO:2) encoded by the nucleotide sequence, structural and functional homologs thereto, including portions thereof, and antibodies thereto.

Also provided are methods for using the foregoing sequences to detect and produce other ones of the sequences, to prevent or treat overproduction of VSMCs, and to prevent or treat proliferative arterial disease and/or vascular restenosis.

BRIEF DESCRIPTION OF THE DRAWINGS

The invention will be described in conjunction with the following drawings in which like reference numerals designate like elements and wherein:

FIG. 4A is the full-length IRT-1 cDNA transcript (SEQ ID NO:1);

FIG. 4B is a hydrophobicity profile of the deduced IRT-1 amino acid sequence;

FIG. 4C is a plot of the alpha helix amphiphilicity of the deduced IRT-1 amino acid sequence;

FIG. 5 is a Northern blot analysis of RNA from rat left common carotid arteries subject to balloon angioplasty probed with a human IRT-1 DNA probe;

DEFINITIONS

Figure 1:
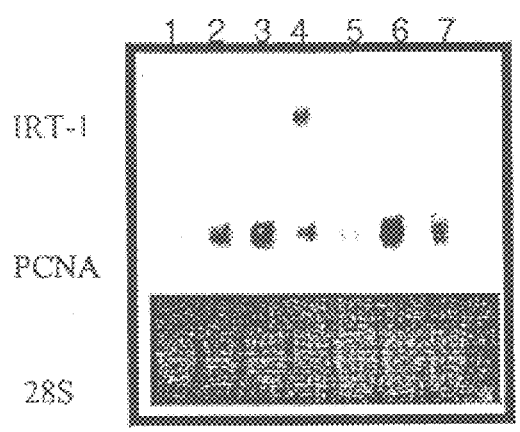
FIG. 1 is a Northern blot analysis showing the expression of IRT-1 in human VSMCs which were (1) serum starved, or treated for 24 hours with (2) fetal calf serum (FCS); (3) Basic Fibroblast Growth Factor (bFGF); (4) Interferon gamma (IFNγ); (5) Interleukin 1 beta (IL-1β); (6) Platelet Derived Growth Factor (PDGF); or (7)Transforming Growth Factor beta (TGFβ).

Although the terminology employed herein generally conforms to conventional usage, the following definitions are provided to remove any doubt as to the meaning of selected terminology employed to help define the limits of the invention.

The term "isolated" means that the chemical moiety in question has been, e.g., synthesized or at least partially purified from its natural state. The term is intended to distinguish the moiety in question from naturally existing forms, and encompasses all other types of forms.

The term "structurally homologous" means that two biopolymers insubstantially differ structurally. Two nucleotide sequences are structurally homologous if, e.g., they differ by a single base substitution. Although there is no fixed homology percentage that absolutely defines whether two sequences are homologous, the homology percentage comparing two sequences can be calculated by various formulas known in the art. References to homology percentages herein are calculated using GenBank software, using algorithms well known to those of ordinary skill in the art. See, e.g., (34), (35) and (36).

The degree of homology between two nucleotide sequences can also be defined by the ability of one of the sequences to hybridize with the perfect complement of the other sequence, under specified hybridization stringency conditions. Two sequences are defined herein as being highly homologous if hybridization occurs under highly stringent hybridization conditions, and are defined as homologous if hybridization occurs under at least moderately high stringency conditions. An example of highly stringent hybridization conditions is hybridization at 4×SSC at 65° C., followed by washing in 0.1×SSC at 65° C. for one hour (16). Another example of highly stringent hybridization conditions is hybridization in 50% formamide, 4×SSC at 55° C. An example of moderately high stringency hybridization conditions is hybridization in 4×SSC at 55° C., followed by washing in 0.1×SSC at 37° C. for one hour. Another example of moderately high stringency hybridization conditions is hybridization in 50% formamide, 4×SSC at 30° C.

The term "functionally homologous" means that two biopolymers insubstantially differ functionally. Two proteins are functionally homologous if, e.g., both bind to the same target. Ordinarily skilled artisans can readily test for functional homology without undue experimentation. For example, immunological testing of proteins provides evidence of functional and structural homology. Functional and structural homology is suggested if an antibody raised against one of the proteins cross-reacts with the other protein.

Two nucleotide sequences are functionally homologous if, e.g., they both encode the same amino acid sequence or homologous amino acid sequences.

DETAILED DESCRIPTION OF PREFERRED EMBODIMENTS

The invention provides a novel isolated nucleotide sequence, IRT-1 (SEQ ID NO:1), structural and functional homologs thereto, including portions thereof, and complements thereto. IRT-1 is an IFNγ-inducible transcript in VSMCs.

IRT-1 was identified as an aberrant PCR product using gene-specific primers and IFNγ-stimulated VSMC RNA as a template (17). Under low-stringency primer annealing conditions, a PCR product almost twice the expected size of AIF-1 was obtained. The DNA sequence of IRT-1 has some sequence similarity to AIF-1, but is a distinct transcript with a distinct expression pattern.

Nucleotide Sequences

The full-length IRT-1 cDNA transcript (SEQ ID NO:1) depicted in FIG. 4A was identified and its expression was characterized in stimulated human VSMCs and balloon angioplasty-injured rat carotid arteries.

The invention is not limited to this nucleotide sequence, but also includes fragments thereof. Since it is preferred that the fragments be uniquely found within IRT-1, and it is conventionally understood that the smallest nucleotide sequences unlikely to be found in more than one segment of the human genome are at least about 18 nucleotides in length, it is preferred in certain embodiments that the fragments of the invention be at least 18 contiguous nucleotides in length, more preferably at least 25 contiguous nucleotides in length. It will be understood by ordinarily skilled artisans, however, that any unique fragment of contiguous nucleotides within IRT-1 is within the scope of the invention. If, for example, it is found that a particular 18 contiguous nucleotide fragment is not unique, the length of the fragment can be incrementally increased one or more contiguous nucleotides at a time until the fragment is unique or sufficiently unique to achieve the desired ends. Thus, this disclosure expressly supports claims to a fragment having any length of contiguous nucleotides from 18 to 1235.

It also will be understood by ordinarily skilled artisans that a plurality of different short fragment lengths can be employed in combination to achieve the same or similar effect as a single type of long fragment. Thus, two fragments from different parts of the complete nucleotide sequence, each being as short as, e.g., 6 contiguous nucleotides each, can be used in combination as probes to specifically detect the presence of the complete sequence's complementary strand in a sample. Such fragments need not be individually unique.

It is particularly preferred that the fragment encode a peptide having IRT-1-like activity, such as, e.g., a peptide comprising an epitope of IRT-1.

In addition to the complete IRT-1 nucleotide sequence and fragments thereof, the invention also encompasses complementary sequences thereto, and homologous sequences structurally and/or functionally homologous to the complete sequence, the fragments and/or the complements. These sequences include DNA, RNA and analogues thereof, including peptide nucleic acids.

In terms of calculated homology percentages, it is preferred that homologous sequences be at least 50% homologous, more preferably at least 70% homologous, and even more preferably, at least 90% homologous to the reference sequence (i.e., to IRT-1, its complements and its fragments), as determined by GenBank software and the algorithms employed thereby (34), (35) and (36).

In terms of hybridization stringency conditions, a homologous sequence is capable of hybridizing with a perfect complement of the reference sequence under moderately high hybridization stringency conditions, and a more preferred highly homologous sequence is capable of hybridizing with a complement of the reference sequence under high stringency hybridization conditions.

Functionally homologous nucleotide sequences encode peptides that are the same or similar to IRT-1 protein. Using the sequence data provided herein, it is within the skill in the art to obtain other nucleotide sequences encoding IRT-1 proteins useful in the invention. Such modifications at the nucleic acid level include, e.g., modifications to the nucleotide sequences which are silent, which change the amino acids without structural or functional effects on the encoded peptide, or which change the amino acids with structural or functional effects on the encoded peptide, e.g., to improve expression or secretion.

As discussed below, the nucleotide sequences of the invention have a variety of diagnostic, prophylactic and therapeutic uses. Advantageously, the nucleotide sequences are useful as diagnostic probes and antisense probes for use in the detection and diagnosis of proliferative arterial disease and vascular restenosis, among other conditions associated with undesirable IRT-1 levels or expression. Oligonucleotide probes of the invention may be useful in such standard diagnostic techniques as Southern blotting and polymerase chain reaction. Alternatively, IRT-1 nucleotide sequences can be used to produce IRT-1 peptides useful in the methods of the invention.

Amino Acid Sequences

The invention also provides a novel isolated amino acid sequence (SEQ ID NO:2) encoded by IRT-1, structural and functional homologs thereto, including portions thereof, and antibodies thereto. The amino acid sequence comprises a strongly basic region at amino acids 67–75, immediately followed by a consensus leucine zipper motif L-x(6)-L-x(6)-L-x-(6)-L-x-(6) at amino acids 75–95. The leucine zipper consists of a periodic repetition of leucine residues at every seventh amino acid over a distance of eight helical turns, existing in an alpha-helical conformation. The IRT-1 protein exhibits a strong alpha helix interaction with a similar alpha helix from a second polypeptide, facilitating dimerization. A single, strongly hydrophobic region is indicated in amino acids 50–80, which may represent a protein binding site. A four amino acid nuclear localization sequence, RPKK (SEQ ID NO:3), is also present at amino acids 25–28. These patterns are present in many gene regulatory proteins, including cAMP response element binding proteins, Jun/AP1 transcription factor family, and Oct-2 octomer binding transcription factor. Other interesting motifs include potential phosphorylation consensus sequences for Mitogen Activated Protein Kinase (MAPK), and Protein Kinase C (PKC), at amino acids 67–70, and 81–83, respectively.

Taken together, these features of the protein make it likely that in human VSMC, IRT-1 protein is involved in IFNγ-driven gene regulation, and the vascular response to injury, and that modulation of IRT-1 activity or expression may represent an attractive target for anti-restenotic modalities.

The invention is not limited to this amino acid sequence, but also includes fragments thereof. Since it is preferred that the fragments be uniquely found within IRT-1 protein, it is preferred in certain embodiments that the fragments of the invention be at least 6 contiguous amino acids in length, more preferably at least 8 contiguous amino acids in length. It will be understood by ordinarily skilled artisans, however, that any unique fragment of contiguous amino acids within IRT-1 protein is within the scope of the invention. If, for example, it is found that a particular 6 contiguous amino acid fragment is not unique, the length of the fragment can be incrementally increased one or more contiguous amino acids at a time until the fragment is unique or sufficiently unique to achieve the desired ends. Thus, this disclosure expressly supports claims to an IRT-1 protein fragment having any length of contiguous amino acids from 6 to 132.

Preferably, the amino acid sequences are biologically active fragments of IRT-1. These functional fragments preferably include at least one epitope of IRT-1.

In addition to the complete IRT-1 protein and fragments thereof, the invention also encompasses antibodies thereof, and homologous sequences structurally and/or functionally homologous to the complete sequence, the fragments and/or the antibodies. For present purposes, the term "antibody" includes both cultured and synthetic ligands that attach to at least one epitope on the amino acid sequence.

Two peptides are herein defined as being homologous to each other if a first one of the peptides immunologically cross-reacts with an antibody raised against the other peptide.

Peptide homologs of the invention preferably possess IRT-1-like biological activity. Examples include polypeptides with minor amino acid variations from the illustrated amino acid sequence of IRT-1 protein (see FIG. 4A and SEQ ID NO:2), in particular, conservative amino acid replacements, wherein amino acids are replaced with amino acids having related side chains and chemical properties. Additionally, IRT-1 peptides of the invention can be modified, for example, to improve production thereof, to enhance protein stability or other characteristics, e.g. binding activity or bioavailability, to enhance their use for screening competitive compounds or to confer some other desired property upon the peptides.

As described in more detail below, the IRT-1 protein and peptide fragments described herein are useful in therapeutic, prophylactic and diagnostic compositions. In addition, they are useful for generating other therapeutic and diagnostic reagents, such as anti-IRT-1 antibodies.

Association With Markers and Toxins

In certain embodiments, it is preferred to modify the nucleic acid and/or amino acid sequences to facilitate their use in diagnosis, prophylaxis and/or therapy. In such embodiments, it is particularly preferred to incorporate into the sequence a marker and/or a toxic agent. Suitable markers and agents, and suitable means for incorporating such moieties into nucleic acid and amino acid sequences are well known in the art. See, e.g., Matthews et al. (17) and the references cited therein.

Recombinant Expression of IRT-1

The nucleotide sequences described herein may be used to produce recombinant IRT-1 amino acid sequences. The resulting amino acid sequences may be used in the methods of the invention, or the method of the invention may involve in vivo expression of the amino acid sequences. To produce the IRT-1 amino acid sequences, the IRT-1 nucleotide sequences may be inserted into a suitable expression system. A recombinant molecule or vector can be constructed in which the cDNA encoding IRT-1 is operably linked to a heterologous expression control sequence permitting expression of the IRT-1 amino acid sequences. Numerous types of appropriate expression vectors and host cell systems are known in the art for mammalian (including human) expression, insect (e.g., baculovirus), yeast, fungal, and bacterial expression, by standard molecular biology techniques.

The transformation of these vectors into appropriate host cells can result in expression of the selected IRT-1 amino acid sequences. Other appropriate expression vectors, of which numerous types are known in the art, can also be used for this purpose.

Suitable host cells or cell lines for transfection by this method include insect cells, such as *Spodoptera frugipedera* (Sf9) cells. Methods for the construction and transformation of such host cells are well-known. See, e.g., Miller et al. (18) and the references cited therein.

Similarly, mammalian cells, such as Human 293 cells, rat aortic vascular cell lines (19), Chinese hamster ovary cells (CHO), the monkey COS-1 cell line or murine 3T3 cells derived from Swiss, Balb-c or NIH mice can be used. Suitable mammalian host cells and methods for transformation, culture, amplification, screening, production and purification are known in the art. See, e.g., U.S. Pat. No. 4,419,446, Gething et al. (20) and Kaufman et al. (21). Another suitable mammalian cell line is the CV-I cell line.

Similarly useful as host cells are bacterial cells. For example, the various strains of *E. coli* (e.g., HB101 and MC1061) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the amino acid sequences useful in the methods of the invention. Other fungal cells may also be employed as expression systems.

Thus, the present invention provides a method for producing a recombinant IRT-1 amino acid sequence which involves transforming a host cell with at least one expression vector containing a recombinant nucleotide sequence encoding an IRT-1 amino acid sequence under the control of a transcriptional regulatory sequence, e.g., by conventional means such as transfection or electroporation. The transformed host cell is then cultured under suitable conditions that allow expression of the IRT-1 amino acid sequence. For example, host cells such as rat aortic vascular smooth muscle cells, can be transfected with sufficient vectors that they are capable of overexpressing the IRT-1 amino acid sequence, making them useful for screening compounds which inhibit IRT-1 expression. In another embodiment, the expressed amino acid sequence is recovered, isolated, and purified from the culture medium (or from the cell, if expressed intracellularly) by appropriate means known to one of skill in the art.

For example, the amino acid sequences can be isolated following cell lysis in soluble form, or extracted in guanidine chloride. If desired, the IRT-1 amino acid sequences of the invention may be produced as a fusion protein. For example, it may be desirable to produce such IRT-1 fusion proteins, to enhance expression of the protein in a selected host cell, or to improve purification. Suitable fusion partners for the IRT-1 proteins described herein are well known to those of skill in the art and include, among others, β-galactosidase and polyhistidine.

Production of Anti-IRT-1 Antibodies

The IRT-1 proteins, as well as modified versions, fragments or analogs thereof, or cells expressing the same, are useful as antigens for the development of antibodies to IRT-1. Antibodies useful in the methods of this invention include monoclonal, polyclonal, chimeric, single chain and humanized antibodies, as well as Fab fragments. These antibodies may be produced by conventional methods, including the Kohler and Milstein hybridoma technique, recombinant techniques such as those described by Huse et al. (22), or any other modifications thereof known to the art. Techniques described for the production of single chain antibodies (see, e.g., U.S. Pat. No. 4,946,778) can be adapted to produce single chain antibodies to the IRT-1 proteins described herein. Also, transgenic mice, or other organisms such as mammals, may be used to express humanized antibodies to a IRT-1 protein or IRT-1-derived protein. The antibodies of this invention may themselves be used to generate anti-idiotype antibodies. Techniques for generating such antibodies are well-known in the art.

The antibodies of the invention may be used in protein form. Alternatively, the antibodies of the invention may be used in the form of a polynucleotide, which expresses the antibody or a functional fragment thereof (e.g., a single chain or a Fab fragment) in vivo.

Diagnostic Reagents

The IRT-1 amino acid sequences, antibodies, and nucleotide sequences (including anti-sense nucleotide sequences) described herein can be used as diagnostic reagents for diagnosing certain vascular disorders, e.g., atherosclerosis, associated with production or excessive production of IRT-1. For example, an IRT-1 protein, antibody, or nucleotide sequence can be used to diagnose vascular damage characteristic of such a condition. These reagents can optionally be labeled using diagnostic labels, such as radioactive labels, calorimetric enzyme label systems and the like conventionally used in diagnostic or therapeutic methods. The reagents can measure IRT-1 levels in selected mammalian tissue in conventional diagnostic assays, e.g., Southern, Northern and Western blotting, polymerase chain reaction and the like. For example, as diagnostic agents, the nucleotide sequences can be employed to detect or quantitate normal IRT-1 mRNA or detect mutations in target gene RNA in a patient sample. Such a method can utilize PCR primers complementary to the nucleotide sequence of FIG. 4A (SEQ ID NO:1). Alternatively, the detection of a specific nucleotide sequence (i.e., IRT-1) can be achieved by methods such as hybridization, RNase protection, chemical cleavage, direct DNA sequencing or the use of restriction enzymes, e.g., restriction fragment length polymorphisms (RFLP) and Southern blotting of genomic DNA. Other suitable assays utilize an IRT-1 protein, protein fragment, or anti-IRT-1 antibody as a reagent. These assays include radioimmunoassays, competitive-binding assays, Western blot analysis and ELISA assays. The selection of the appropriate assay formal and label system is within the skill of the art and may readily be chosen without requiring additional explanation by resort to the wealth of art in the diagnostic area.

Thus, the present invention provides methods for the use of these IRT-1 protein, antibody or nucleotide sequence reagents in the diagnosis of disorders characterized by vascular restenosis, such as atherosclerosis. The methods may involve contacting a selected sample, e.g., blood, plasma, serum, or other suitable cells, with the selected reagent, protein, antibody or nucleotide sequence, and measuring or detecting the amount of IRT-1 present in the sample in a selected assay format based on the binding or hybridization or the reagent to the sample.

Prophylactic and Therapeutic Reagents

The invention further provides methods for treatment and prevention of conditions associated with proliferation of VSMCs, such as vascular restenosis. Certain embodiments of these methods comprise administration of an anti-IRT-1 antibody for blocking IRT-1 activity in a tissue. Also useful as therapeutic reagents of this invention are anti-idiotype antibodies, which can be used to block binding of IRT-1 to its corresponding receptor.

In other embodiments, the therapeutic reagent can be an IRT-1 nucleotide sequence, a vector containing the nucleotide sequence or an IRT-1 amino acid sequence. Alternatively, the therapeutic reagent can be a drug obtained using the methods described below.

The therapeutic reagents can be administered by appropriate routes in a pharmaceutically acceptable composition. Generally, the composition contains about 10 μg to about 10 mg of the active agent (e.g., anti-IRT-1 antibody, or a vector or nucleotide sequence described herein) per kg body weight. It will be appreciated that optimum dosage may be adjusted by one skilled in the art, taking into account the indication, its severity, route of administration, and the like.

Suitable pharmaceutical carriers are well known to those of skill in the art and can be readily selected from, e.g., saline, buffered saline, dextrose, water, glycerol, ethanol, and combinations thereof. The pharmaceutical compositions of the invention may optionally contain other active ingredients, or other desirable components, such as, e.g., pH adjusters, preservatives, and the like.

Appropriate delivery routes may be readily determined by one of skill in the art and include, for example, intravenous, intramuscular, subcutaneous, intraperitoneal, interdermal, oral, vaginal, anal, intranasal, and topical routes. Currently, the preferred method of delivery is intravenous. However, one of skill in the art can readily select other appropriate routes of administration. Dosing may be repeated as needed or desired.

Drug Screening and Development

The present invention also provides methods for using the IRT-1 proteins, antibodies and nucleotide sequences described herein in the screening and development of chemical compounds or proteins which have utility as therapeutic drugs for the treatment of atherosclerosis and other vascular disorders.

For example, such a compound is capable of binding to IRT-1 and either enhancing (acting as an agonist) or blocking (acting as an antagonist) its biological activity. Such compounds are anticipated to be useful as a drug component for the treatment or prevention of vascular disorders, as described above. Presently, conventional assays and techniques exist for the screening and development of drugs capable of competitively binding to selected regions of IRT-1. These include the use of phage display system for expressing the IRT-1 protein or portions thereof and using a culture of transfected E. coli or another microorganism to produce the proteins for binding studies of potential binding compounds. See, for example, the techniques described by Cesarini (23), Gram et al. (24) and Summer et al. (25).

Other conventional drug screening techniques may be employed using the proteins, antibodies or nucleotide sequences useful in this aspect of the invention. For example, a method for identifying compounds which specifically bind to IRT-1 nucleotide sequences can include simply the steps of contacting a selected IRT-1 nucleotide sequence fragment with a test compound to permit binding of the test compound to the nucleotide sequence fragment; and determining the amount of test compound, if any, which is bound to the nucleotide sequence fragment. Such a method may involve the incubation of the test compound and the IRT-1 nucleotide sequence fragment immobilized on a solid support.

Another method of identifying compounds which specifically bind to IRT-1 sequences can include the steps of contacting an IRT-1 nucleotide sequence fragment immobilized on a solid support with both a test compound and the protein sequence which is a receptor for IRT-1 to permit binding of the receptor to the IRT-1 nucleotide sequence fragment; and determining the amount of the receptor which is bound to the nucleotide sequence fragment. The inhibition of binding of the normal protein by the test compound thereby indicates binding of the test compound to IRT-1.

IRT-1-like effects of potential agonists, or the effects of potential antagonists, can be measured by, e.g., determining the activity of a reporter system following interaction of the candidate molecule with a cell or appropriate cell preparation, and comparing the effect with that of IRT-1 or molecules that are found to elicit the same effects as IRT-1. Reporter systems that may be useful in this regard include but are not limited to "calorimetric" labeled substrate converted into product, a reporter gene that is responsive to changes in IRT-1 activity and binding assays known in the art. Other suitable methods are well known to those of skill in the art. Thus, through use of such methods, the present invention provides compounds capable of interacting with IRT-1 nucleotide sequences, amino acid sequences or portions thereof, and either enhancing or decreasing its biological activity, as desired. Such compounds are encompassed by this invention.

Methods

As discussed above, the invention also provides methods for using the nucleic acid and amino acid sequences of the invention to detect and produce other ones of the compounds, to prevent or treat overproduction of VSMCs, and to prevent or treat conditions associated with proliferation of VSMCs, including vascular restenosis.

As the compounds of the invention are capable of stopping overproduction of VSMCs, the invention also provides methods for studying, detecting, preventing and/or treating overproliferation of cells. Accordingly, the invention may be used to study, diagnose, prevent and treat cancer.

The invention will be illustrated in more detail with reference to the following Examples, but it should be understood that the present invention is not deemed to be limited thereto.

EXAMPLES

MATERIALS AND METHODS

Rat Left Common Carotid Artery Balloon Angioplasty

Left common carotid artery balloon angioplasty was performed on 350 g male Sprague-Dawley rats (Charles River Breeding Laboratory Inc., Wilmington, Mass.) under sodium pentobarbital anesthesia (65 mg/kg, i.p.; Steris Laboratories, Phoenix, Ariz.) as described previously (26). Briefly, the left external carotid artery was cleared of adherent tissue, allowing the insertion of an 2-F Fogarty arterial embolectomy catheter (Model 12-060-2F; Baxter Healthcare, Santa Ana, Calif.). The catheter was guided a fixed distance down the common carotid artery to the aortic arch, inflated with a fixed volume of fluid and withdrawn back to the site of insertion a total of three times. Once completed, the catheter was removed and the wound closed (9 mm Autoclips; Clay Adams) and swabbed with Povadyne surgical scrub (7.5% Povidone-Iodine; Chaston, Danville, Conn.). Animals were housed in Plexiglas cages under a twelve hour light/dark cycle with access to standard laboratory chow and drinking water ad libitum until required for tissue collection.

To isolate the carotid arteries, rats were exsanguinated via the vena cava under barbiturate anesthesia (100 mg/kg, i.p.). Left common carotid arteries were rapidly cleared of adherent tissue in situ, isolated and placed directly in guanidine thiocyanate (Promega Co., Madison, Wis.). These vessels were then immediately processed for RNA isolation. For subsequent Northern analysis, tissues were isolated from naive animals (control) and from animals that had undergone angioplasty one, three and seven days prior, and RNA extracted as described in a following section. Northern analysis was also performed on sham vessels (data not shown). All surgical procedures were performed in accordance with the guidelines of the Animal Care and Use Committee of Deborah Research Institute and the American Association for Laboratory Animal Care.

Cells and Culture

Human VSMCs were obtained as cryopreserved secondary culture from Clonetics Corporation (San Diego, Calif.) and subcultured in growth medium as described previously (26). The growth media were changed every other day until the cells approached confluence. Cells from passage 5-9 were used in the described studies. Pre-confluent VSMCs were serum starved for 48 hours in Dubecco's minimum essential media, then exposed for 20 hours to 10% fetal calf serum (FCS), 10 ng/ml basic Fibroblast Growth Factor (bFGF), 100 u/ml Interferon gamma (IFNγ) 20 ng/ml Interleukin 1 beta (IL-1β), 20 ng/ml Platelet Derived Growth Factor (PDGF), or 2 ng/ml Transforming Growth Factor beta (TGFβ) for 20 hours, at which times samples were processed for RNA isolation. Some samples remained untreated and were used as controls. PDGF, bFGF, IFNγ, and TGFβ were purchased from GIBCO-BRL, (Bethesda, Md.), and IL-1β was purchased from Boehringer Mannheim (Indianapolis, Ind.). Human peripheral blood lymphocytes (PBL) were isolated by venipuncture from normal adult donors, isolated by Ficoll-Hypaque density-gradient centrifugation and cultured in DMEM/CM phytohemagglutinin A (PHA) (2.5 μg/ml) (purchased from Pharmacia) for the times indicated, and processed for RNA isolation.

5' RACE Analysis

Total RNA was isolated from IFNγ-stimulated human VSMC as described above and reverse transcribed using oligo dT primer and Superscript II purchased from Gibco-BRL according to the manufacturer's protocol. Transcripts were poly C tailed with terminal deoxytransferase, and 5' cDNA amplified by PCR of dC-tailed cDNA using nested IRT-1-specific reverse primers. PCR products were isolated from agarose gels by glass extraction and cloned into the PCRII plasmid (Invitrogen) for DNA sequence analysis.

DNA Sequencing and Sequence Analysis

The cDNA clone obtained above was dideoxy nucleotide sequenced on both strands in its entirety (Sequenase, United States Biochemical Corporation) as previously described (27). DNA and protein sequences were analyzed using the Mac Vector software package (International Biotechnologies, Inc.). Searches for sequence similarity were performed using the GenBank Nucleic Acid database, and Prosite protein database through the Genetics Computer Group FASTA, BLAST, PROSITE, and PSORT programs.

RNA Isolation and Northern Blot Analysis

For each time point studied, four or five left carotid arteries were pooled, or VSMC from culture isolated and total RNA obtained by standard techniques as described (26). Equal amounts of RNA were loaded and separated on a 1.3% agarose/formaldehyde gel, transferred to nitrocellulose, and hybridized (0.25 M NaCl, 1% sodium dodecyl sulfate, 50% formamide, 2×Denhardt's solution, 25 µg denatured salmon sperm DNA and 5% dextran sulphate at 42° C. overnight) with the indicated probe. All probes were [$\alpha^{32}P$]-labeled by the random priming method (Boehringer Mannheim, Indianapolis, Ind.) (all isotopes were from Amersham Inc., Arlington Heights, Ill.). Blots were washed under high stringency (0.2×sodium citrate, 0.1% sodium dodecyl sulfate, 65° C.), and exposed to film for 6–48 hr. at 80° C. The same filter was stripped and subsequently hybridized with the various DNA probes. The beta actin probe was generated from PCR amplimers (Clonetech, Palo Alto, Calif.). Relative intensities of hybridization signals were obtained by densiometric scanning (RFLP-Scan Software, Scanalytics, Inc.) of autoradiograms exposed within the linear range of the film (Kodak X-OMAT). Human multiple tissue Northern blots were purchased from Clonetech, Inc. (Palo Alto, Calif.), hybridized, and washed according to manufacturer's instructions.

RESULTS

Under low-stringency primer annealing conditions, an aberrant PCR product almost twice the expected size of AIF-1 was observed only from RNA isolated IFNγ-stimulated human VSMC (data not shown). Using this PCR product as a probe, the expression of IRT-1 in cytokine-driven VSMC was investigated by performing Northern analysis on human VSMC which were serum-starved for 48 hours, then stimulated for 20 hours with a variety of cytokines.

FIG. 1 shows that the expression of human IRT-1 mRNA in VSMCs is induced by IFNγ. VSMC were serum-starved for 48 hours, and 15 µg total RNA isolated from: 1) serum starved, and VSMC treated for 24 hours with 2) 10% FCS, 3) bFGF, 4) IFNγ, 5) IL1-β, 6) PDGF, and 7) TGFβ. Total RNA was separated on a 1.3% agarose/formaldehyde gel, transferred to nitrocellulose, and hybridized with the selected probe. The same filter was stripped and sequentially hybridized with probes for the respective genes as shown, and the probes were exposed to film overnight. FIG. 1 shows that the IRT-1 transcript is approximately 1300 nucleotides in length, and is expressed in human VSMC only upon treatment with IFNγ, indicating that IRT-1 is an IFNγ-specific transcript in these cells.

Figure 2:
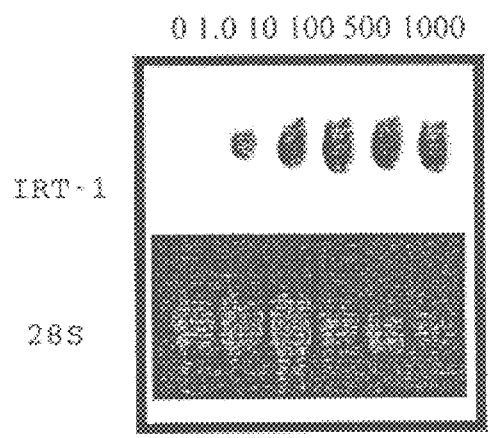
FIG. 2 is a Northern blot analysis showing the expression of IRT-1 in human VSMCs which were unstimulated, or stimulated with IFNγ at a concentration of 1.0 U/ml, 10 U/ml, 100 U/ml, 500 U/ml, or 1000 U/ml.

It was important to optimize conditions for expression of this transcript. FIG. 2 indicates that IRT-1 expression is dose-dependent, with optimal concentrations of IFNγ being 100 U/ml. VSMC were serum-starved for 48 hours, and 15 µg total RNA isolated from 1) unstimulated, 2) 1.0 U/ml, 3) 10 U/ml, 4) 100 U/ml, 5) 500 U/ml, and 6) 1000 U/ml IFNγ, was separated on a 1.3% agarose/formaldehyde gel, transferred to nitrocellulose, and hybridized with the selected probe. The probes were exposed to film overnight.

Figure 3A:
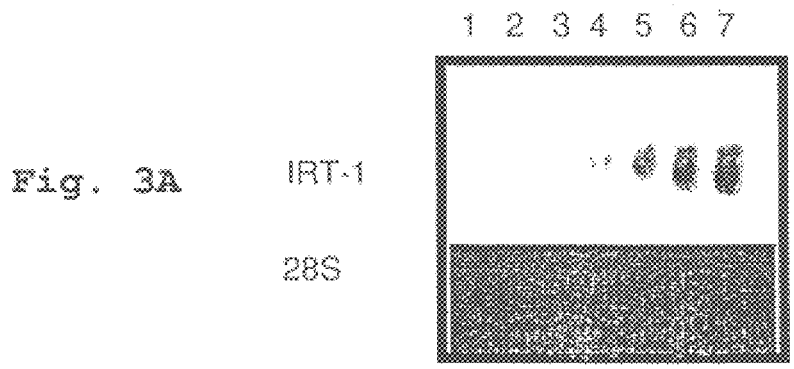
FIG. 3A is a Northern blot analysis showing the time course of expression of IRT-1 in IFNγ (100 U/ml)-stimulated human VSMCs. RNA was isolated from (1) unstimulated cells, or from stimulated cells at (2) 4 hours, (3) 8 hours, (4) 16 hours, (5) 24 hours, (6) 72 hours, or (7) 5-days post stimulation.
Figure 3B:
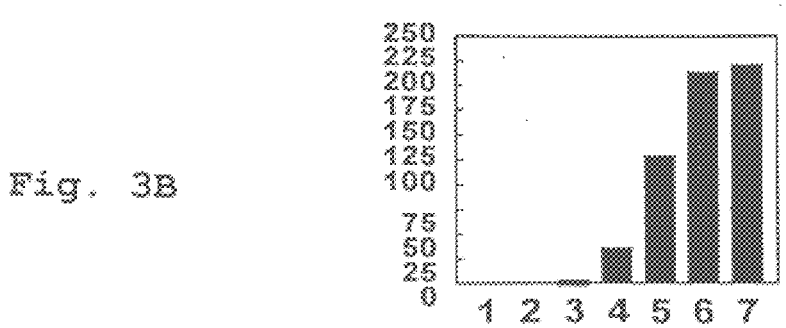
FIG. 3B is a densiometric analysis of IRT-1 expression in IFNγ-stimulated VSMC.

FIGS. 3A and 3B show the time course of IRT-1 mRNA expression in IFNγ-stimulated human VSMC. VSMC were serum-starved for 48 hours, and 15 µg total RNA isolated from 1) unstimulated, 2) 4 hours, 3) 8 hours, 4) 16 hours, 5) 24 hours, 6) 72 hours, and 7) 5 days, with 100 U/ml IFNγ, was separated on a 1.3% agarose/formaldehyde gel, transferred to nitrocellulose, and hybridized with the selected probe.

FIG. 3B is a densiometric analysis of IRT-1 expression in IFNγ-stimulated VSMC. Values expressed are displayed as the relative level of expression normalized to 28S RNA. FIGS. 3A and 3B show that IRT-1 expression is time-dependent, beginning at approximately 8 hours post IFNγ treatment, and reaching a peak at 72 hours post IFNγ treatments.

The full-length IRT-1 transcript was determined by the rapid amplification of cDNA ends (RACE) procedure using IRT-1-specific primers. As shown in FIG. 4A, the full-length IRT-1 cDNA transcript (SEQ ID NO:1) is approximately 1.3 kB, and following termination codons in all three reading frames, contains on open reading frame of 399 nucleotides encoding for a deduced 132 amino acid basically-charged protein with a mass of approximately 14,617 Dalton.

The deduced amino acid sequence of human IRT-1 hints at its functionality. A strongly basic region at amino acids 67–75 is immediately followed by a consensus leucine zipper motif, L-x(6)-L-x(6)-L-x(6)-L-x(6), at amino acids 75–95 (underlined in FIG. 4A). The leucine zipper consists of a periodic repetition of leucine residues at every seventh amino acid over a distance of eight helical turns, existing in an alpha-helical conformation.

FIG. 4C shows that the alpha helix amphiphilicity of the deduced IRT-1 amino acid sequence may facilitate dimerization with a second amino acid sequence. FIG. 4B is a hydrophobicity profile of the deduced IRT-1 amino acid sequence according to the method of Kyte and Doolittle. A single, strongly hydrophobic region is indicated in amino acids 50–80, which may represent a protein binding site. As shown in FIG. 4A, a four amino acid nuclear localization sequence, RPKK, is also present at amino acids 25–28 (boxed area in FIG. 4A). These patterns are present in many gene regulatory proteins, including cAMP response element binding proteins, Jun/AP1 transcription factor family, and Oct-2 octomer binding transcription factor. Other interesting motifs include potential phosphorylation consensus sequences for Mitogen Activated Protein Kinase (MAPK), and Protein Kinase C (PKC), at amino acids 67–70, and 81–83, respectively (bolded in FIG. 4A).

Human vascular smooth muscle cells which over-express IRT-1 protein proliferate at a dramatically slower rate than do cells which do not express IRT-1 protein. The protein coding region of the IRT-1 cDNA was cloned by PCR using IRT-1 gene-specific primers. The 5' PCR primer also contained a genetic sequence known to enhance protein expression. This sequence, (GCCGCCGCCATGG) (SEQ ID NO:4) is known as the Kozak consensus sequence (37). This modified protein coding sequence was inserted into the expression vector pBK-CMV (Stratagene, Inc.) and purified DNA from a single bacterial colony containing IRT-1 in pBK-CMV was isolated.

Human vascular smooth muscle cells were transfected with either pBK-CMV plasmid alone or with plasmid pBK-CMV containing IRT-1. Transfection was performed using LipofectAMINE reagent (Life Technologies, Inc.) mixed with the DNA to facilitate transfection of the DNA into the cell. This procedure allows the DNA to be incorporated into the host cell's chromosomes. Two days following transfection, the compound G418 (Geneticin) was added to the cells. G418 kills cells which do not contain the pBK-CMV plasmid, leaving only cells containing pBK-CMV or IRT-1 in pBK-CM. Such transfected cells, along with cells not containing any transfected DNA, were seeded into tissue culture flasks at equal densities and left to grow in the presence of growth medium +G418 for 14 days.

After 14 days, the cells were then trypsinized and counted using a hemocytometer to look for differences in proliferation. At 14 days, cell counts for pBK-CMV containing cells were $6.48 \times 10^5$ and cell counts for IRT-1/pBK-CMV containing cells were $3.1 \times 10^4$. This amount is 20 fold less than in cells not over-expresssing IRT-1 protein. Flasks containing cells which were not transfected with DNA did not yield any cells. Results of similar experiments yielded similar numbers, with IRT-1 containing cells resulting in a 15 and 22% decrease in cells compared with control cells.

The data clearly show that over-expression of IRT-1 protein in human vascular smooth muscle cells has an anti-proliferative effect on these cells.

Because activated VSMCs are the major cellular component of damaged arteries, total RNA from undamaged and from rat carotid arteries was isolated at three time points following balloon angioplasty. Northern analysis was performed using the insert of this clone as a hybridization probe. FIG. 5 shows a Northern analysis of RNA from rat left common carotid arteries subject to balloon angioplasty prior to, and 1, 3, and 7 days following balloon angioplasty (lanes 1, 2, 3, and 4, respectively) probed with a human IRT-1 DNA probe. Total RNA (10 µg) from rat carotid arteries was separated on a 1.3% agarose/formaldehyde gel, transferred to nitrocellulose, hybridized, and washed as described in the methods. A beta actin probe was used as a loading control.

Scanning densiometric analysis of this blot normalized to beta actin content demonstrates an 8-fold increase in expression of IRT-1 mRNA over basal levels 1 day post balloon angioplasty, 4-fold at 3 days, and 2-fold at 7 days post-injury. This expression pattern indicates that expression of this gene is induced in rat carotid arteries in response to vascular injury caused balloon angioplasty.

Figure 6:
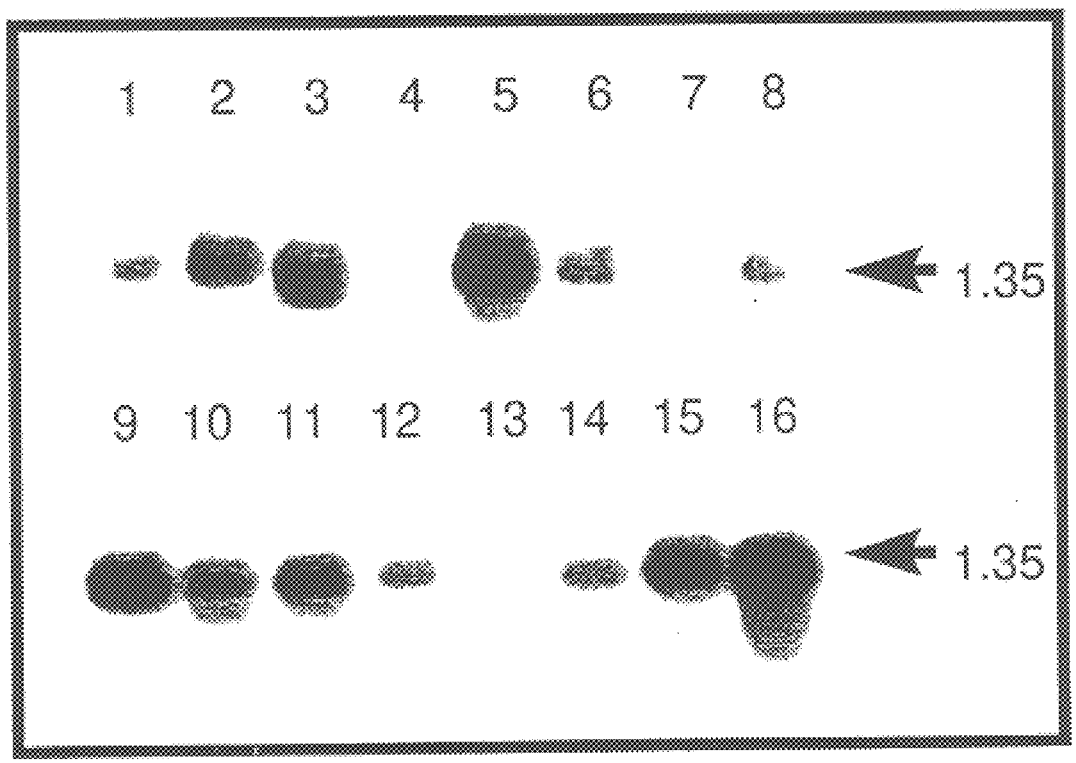
FIG. 6 is a Northern blot analysis of human tissue distribution of human IRT-1 mRNA expression.

FIG. 6 shows a Northern analysis of human tissue distribution of human IRT-1 mRNA expression. Two µg poly A+ mRNAs from 1) pancreas, 2) kidney, 3) skeletal muscle, 4) liver, 5) lung, 6) placenta, 7) brain, 8) heart, 9) peripheral blood lymphocyte, 10) colon, 11) small intestine, 12) ovary, 13) testes, 14) prostrate, 15) thymus, and 16) spleen were hybridized with each respective probe as described in above. The respective size of the transcript is 1.35 KB, and size standards in KB are indicated by numbers on the right of the figure. The blot was purchased from Clonetech, Inc. La Jolla, Calif. The probe was exposed to film overnight.

IRT-1 mRNA is expressed in a variety of human tissues, with the highest expression in cells of lymphoid origin, in particular, spleen, peripheral blood (PBL), and thymus. Other tissues expressing appreciable amounts of IRT-1 are lung, skeletal muscle, and small intestine. Detectable amounts of expression are in pancreas, kidney, liver, placenta, heart, colon, ovary, testes and prostate. No IRT-1 mRNA is detectable in brain. The relatively high degree of constitutive expression of IRT-1 in human lymphoid tissue suggests a function for this protein in cells of this lineage, and led to an investigation of the expression of IRT-1 in activated human lymphocytes.

Figure 7:
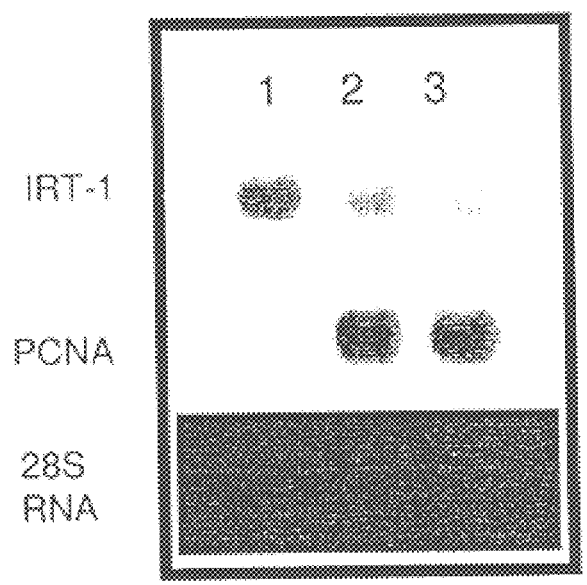
FIG. 7 is a Northern blot analysis of human peripheral blood lymphocytes isolated from a normal human donor.

Northern analysis of the IRT-1 transcript in unstimulated, and phytohemagluttin A (PHA)-stimulated human PBL is revealing. FIG. 7 shows PBL isolated from a normal human donor untreated (lane 1), or stimulated with 5 µg/ml of PHA for 24 or 72 hours (lanes 2 and 3). Ten µg total RNA was separated on a 1.3% agarose/formaldehyde gel, transferred to nitrocellulose, and hybridized with the selected probe. The same filter was stripped and sequentially hybridized with probes for the respective mRNAs as shown.

FIG. 7 shows that unstimulated PBL demonstrate a high level of constitutive IRT-1 expression, consistent with that observed in the multiple tissue analysis (FIG. 6). However, 24 hour treatment of these cells with PHA decreases IRT-1 mRNA levels over three-fold, and 72 hour treatment results in a six-fold decrease in IRT-1 mRNA levels. PCNA levels in such treated cells are increased dramatically, reflecting the proliferative state of these cells. These results indicate that the constitutive levels of IRT-1 mRNA expression in human PBL can be diminished by the lymphocyte mitogen PHA.

Immune cells are present in the atherosclerotic lesion, and appear in greater numbers immediately following balloon angioplasty-induced vascular injury (28). IFNγ is produced in vivo by activated T lymphocytes, and a number of studies have determined that T lymphocytes exert phenotypic and proliferative effects on VSMC (12,29). It has been shown that IFNγ inhibits proliferation of VSMC in culture, and IFNγ inhibits arterial restenosis post-balloon angioplasty (11-13,30,31). Therefore, identification and characterization of IFNγ-specific transcripts in VSMC are a promising strategy to discern and control the molecular mechanisms underlying vascular proliferative disease.

Sequence similarity searches using the IRT-1 nucleic acid sequence yielded no significant matches to expressed sequences in genetic databases. However, over 95% homology exists between the 1235 base sequence of IRT-1 cDNA and an intronic region of the human MHC class III B Cell Activation Transcript (BAT-2) (32,33). However, there is no homology at all in the cDNA sequence, or at the protein level between the two. Since the BAT-2 sequence is intronic, it is not transcribed into mRNA nor expressed as protein. Therefore, IRT-1 is a novel transcript.

IRT-1 mRNA is constitutively expressed in a number of human tissues, but is expressed in human VSMC only when they are stimulated with IFNγ (unlike, e.g., AIF-1, which is constitutively expressed at low levels and its expression increases only moderately in response to any number of different cytokines). In human VSMC, IRT-1 mRNA is induced over two hundred fold 72 hours after IFNγ treatment, but is reduced six fold in PHA-stimulated human PBL. This suggests a constitutive role in maintenance of the Elymphocyte phenotype and an inducible role in IFNγ-driven VSMC activation. IRT-1 encodes a protein including a strongly basic region, a core nuclear localization sequence, and a leucine zipper motif. Taken together, these regions make it likely that in human VSMC, IRT-1 protein is involved in IFNγ-driven gene regulation, and the vascular response to injury, and that modulation of IRT-1 activity or expression may represent an attractive target for anti-restenotic modalities.

While the invention has been described in detail and with reference to specific examples thereof, it will be apparent to one skilled in the art that various changes and modifications can be made therein without departing from the spirit and scope thereof.

SCIENTIFIC JOURNAL BIBLIOGRAPHY

1. Libby et al., "A cascade model for restenosis: a special case of atherosclerosis progression," *Circulation* 86:III-47–III-52 (1992).
2. Ross, "The pathogenesis of atherosclerosis: a perspective for the 1990s," *Nature* 362:801–809 (1993).
3. O'Brien et al., "Proliferation in primary and restenotic coronary atherectomy tissue," *Circ. Res.* 73:223–231 (1993).
4. Clowes et al., "Mechanisms of stenosis after arterial injury," *Lab. Invest.* 49:208–215 (1983).
5. Liu et al., "Restenosis after coronary angioplasty: potential biologic determinants and role of intimal hyperplasia," *Circulation* 79:1374–1380 (1989).
6. Austin et al., "Intimal proliferation of smooth muscle cells as an explanation for recurrent coronary artery stenosis after percutaneous transluminal coronary angioplasty." *J. Am. Coll. Cardiol.* 6:369–375 (1985).
7. Schwartz et al., "Restenosis after balloon angioplasty: a practical proliferative model in porcine coronary arteries," *Circulation* 82:2190–2200 (1990).
8. Nilsson, "Cytokines and smooth muscle cells in atheroslerosis," *Cardiovasc Res* 27:1184–1189 (1992).
9. Tanaka et al., "Cytokine gene regulation: regulatory cis-elements and DNA binding factors involved in the interferon system," *Adv. Immunol.* 52:263–281 (1992).
10. Demaeyer et al., Interferons and other regulatory cytokines (John Wiley and Sons, N.Y., 1988).
11. Hansson et al., "T lymphocytes inhibit the vascular response to injury," *Proc. Natl. Acad. Sci. USA* 88:19530–10534 (1991).
12. Rolfe et al., "T lymphocytes affect smooth muscle cell Aphenotype and proliferation," *Arterioscler. Thromb. Vasc. Biol.* 15:1204–1210 (1995).
13. Nunokawa et al., "Interferon-γ inhibits proliferation of rat vascular smooth muscle cells by nitoric oxide generation," *Biochem. Biophys. Res. Comm.* 188:409–415 (1992).
14. Tanaka et al., "Recognition DNA sequences of Interferon Regulatory Factor 1 (IRF-1) and IRF-2, Regulators of Cell growth and the Interferon system," *Mol. Cell Bio.* 13:4531–4538 (1993).
15. Wang et al., "Interferon Regulatory Factors and TFIIB cooperatively regulate Interferon-responsive promoter activity in vivo and in vitro," *Mol. Cell Bio.* 16:6313–6324 (1996).
16. T. Maniatis et al., *Molecular Cloning (A Laboratory Manual)*, pp. 387–89 (Cold Spring Harbor Laboratory, 1982).
17. Matthews et al., "Analytical Strategies for the Use of DNA Probes," *Anal. Biochem.* 169: 1–25 (1988).
18. Miller et al., *Genetic Engineering* 8:277–298 (Plenum Press 1986).
19. Holstein et al., *Eur. J. Pharmacol.—Mol. Pharmacol. Section* 225:347–350 (1992).
20. Gething et al., *Nature* 293:620–625 (1981).
21. Kaufman et al., *Mol. Cell. Biol.* 5(7):1750–1759 (1985).
22. Huse et al., *Science* 246:1275–1281 (1988).
23. Cesarini, *FEBS Letters* 307(1):66–70 (1992).
24. Gram et al. *J. Immunol. Meth.* 161:169–176 (1993).
25. C. Summer et al., *Proc. Natl. Acad. Sci. USA* 89:3756–3760 (1992).
26. Autieri et al., "cDNA cloning of human Allograft Inflammatory Factor-1: tissue distribution, cytokine induction, and mRNA expression in injured rat carotid arteries," *Biochem. Biophys. Res. Comm.* 228:29–37 (1996).
27. Autieri et al., "Use of Differential Display to Identify Differentially Expressed mRNAs Induced by Rat Carotid Artery Balloon Angioplasty," *Lab. Invest.* 72:656–671 (1995).
28. Hansson et al., "Immune mechanisms in atherosclerosis," *Arteriosclerosis* 9:567–578 (1989).
29. Wang et al. "T-cell lymphokines, Interleukin-4, and Gamma Interferon, modulate the induction of vascular smooth muscle tissue plasminogen activator and migration by serum and Platelet-Derived Growth Factor," *Circ. Res.* 77:1095–1106 (1995).
30. Hansson et al., "Interferon γ inhibits arterial sentosis after injury," *Circulation* 84:1266–1271 (1991).
31. Castronuovo et al., "Cytokine therapy for arterial restenosis: inhibition of neointimal hyperplasia by gamma-interferon," *Cardiovascular Surgery* 3:463–468 (1995).
32. Banerji et al., "A gene pair from the human major histocompatibility complex encodes large proline-rich proteins with multiple repeated motifs and a single ubiquitin-like domain," *Proc. Natl. Acad. Sci. USA* 78:2374–2378 (1990).
33. Iris et al., "Dense Alu clustering and a potential new member of the NF-KB family within a 90 kilobase HLA class III segment," *Nature Genetics* 3:137–145 (1993).
34. Altschul et al., "Basic local alignment search tool," *J. Mol. Biol.* 215:403–410 (1990).
35. Gish et al., "Identification of protein coding regions by database similarity search," *Nature Genetics* 3:266–272 (1993).
36. Karlin et al., "Methods for assessing the statistical significance of molecular sequence features by using general scoring schemes," *Proc. Natl. Acad. Sci. USA* 90:5873–5877 (1993).
36. Kozak, "Analysis of 5' noncoding sequences from 699 vertebrate messenger RNAs," *Nucleic Acids Research*, 15:8125–8148 (1987).

What is claimed is:

1. An isolated nucleic acid sequence of approximately 1.3 kilobases or less encoding a peptide that inhibits vascular smooth muscle cell proliferation, comprising:

(a) nucleotides 454 to 852 of SEQ ID NO:1;

(b) the sequence complementary to (a); or (c) a nucleotide sequence capable of hybridizing to (a) or (b) in 4×SSC at 65° C., followed by washing in 0.1×SSC at 65° C. for one hour.

2. An isolated nucleic acid according to claim 1 comprising nucleotides 454 to 852 of SEQ ID NO:1.

3. An isolated nucleic acid according to claim 1 comprising SEQ ID NO:1.

4. An isolated nucleic acid sequence encoding a polypeptide comprising the amino acid sequence SEQ ID NO:2.

5. An expression vector comprising the nucleotide sequence of claim 1 operably linked to a heterologous expression control sequence.

6. An expression vector comprising the nucleotide sequence of claim 4 operably linked to a heterologous expression control sequence.

7. A method for producing a polypeptide having the amino acid sequence SEQ ID NO:2, said method comprising expressing the vector of claim 5 in a host cell.

8. A method for producing a polypeptide having the amino acid sequence SEQ ID NO:2, said method comprising expressing the vector of claim 6 in a host cell.

9. A host cell transformed with the vector of claim 5.

10. A host cell transformed with the vector of claim 6.

11. The nucleotide sequence of claim 1, further comprising a marker or toxin attached thereto.

* * * * *